(12) United States Patent
Petersen et al.

(10) Patent No.: US 10,474,002 B2
(45) Date of Patent: Nov. 12, 2019

(54) GENERATION OF HIGH ENERGY MID-INFRARED CONTINUUM LASER PULSES

(71) Applicant: Cornell University, Ithaca, NY (US)

(72) Inventors: Poul B. Petersen, Ithaca, NY (US); Ashley Stingel, Ithaca, NY (US)

(73) Assignee: Cornell University, Ithaca, NY (US)

(*) Notice: Subject to any disclaimer, the term of this patent is extended or adjusted under 35 U.S.C. 154(b) by 142 days.

(21) Appl. No.: 15/738,522

(22) PCT Filed: Jun. 27, 2016

(86) PCT No.: PCT/US2016/039664
§ 371 (c)(1),
(2) Date: Dec. 20, 2017

(87) PCT Pub. No.: WO2016/210444
PCT Pub. Date: Dec. 29, 2016

(65) Prior Publication Data
US 2018/0180969 A1 Jun. 28, 2018

Related U.S. Application Data

(60) Provisional application No. 62/184,846, filed on Jun. 25, 2015.

(51) Int. Cl.
*G02F 1/35* (2006.01)
*G02F 1/39* (2006.01)
(Continued)

(52) U.S. Cl.
CPC ............. *G02F 1/353* (2013.01); *G01N 21/35* (2013.01); *G02F 1/3501* (2013.01);
(Continued)

(58) Field of Classification Search
CPC ...... G02F 1/353; G02F 1/3536; G02F 1/3511; G02F 1/3501; G02F 1/3525;
(Continued)

(56) References Cited

U.S. PATENT DOCUMENTS

2003/0110810 A1  6/2003  Dunn et al.
2006/0210227 A1  9/2006  Shaw et al.
(Continued)

FOREIGN PATENT DOCUMENTS

KR  100300822 B1  9/2001

OTHER PUBLICATIONS

Stingel et al. ("Covering the vibrational spectrum with microjoule mid-infrared supercontinuum pulses in nonlinear optical applications", Journal of Optical Society of America vol. 34, No. 6 Jun. 2017) (Year: 2017).*

(Continued)

*Primary Examiner* — David P Porta
*Assistant Examiner* — Meenakshi S Sahu
(74) *Attorney, Agent, or Firm* — Perkins Coie LLP

(57) ABSTRACT

In one aspect, a method is provided for generating supercontinuum laser pulses within a continuous mid-infrared spectral range in a chalcogenide material. This method includes focusing an input laser beam of femtosecond pulses with a pulse energy higher than 10 microjoule along an optical path of the input laser beam; placing a chalcogenide material at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material; and simultaneously mov- (Continued)

ing the chalcogenide material laterally relative to the input laser beam to avoid damage to the chalcogenide material.

26 Claims, 10 Drawing Sheets

(51) Int. Cl.
G01N 21/35 (2014.01)
G02F 1/355 (2006.01)

(52) U.S. Cl.
CPC .......... *G02F 1/3511* (2013.01); *G02F 1/3525* (2013.01); *G02F 1/3536* (2013.01); *G02F 1/3555* (2013.01); *G02F 1/39* (2013.01); G01N 2201/06113 (2013.01); G02F 2001/3503 (2013.01); G02F 2001/3528 (2013.01); G02F 2001/392 (2013.01); G02F 2203/11 (2013.01)

(58) Field of Classification Search
CPC .... G02F 1/3555; G02F 1/39; G02F 2001/392; G02F 2001/3503; G02F 2203/11; G02F 2001/3528; G01N 21/35; G01N 2201/06113
See application file for complete search history.

(56) References Cited

U.S. PATENT DOCUMENTS

| | | | |
|---|---|---|---|
| 2012/0236314 A1* | 9/2012 | Fermann | G02F 1/365 356/479 |
| 2013/0188240 A1 | 7/2013 | Shaw et al. | |
| 2015/0160532 A1* | 6/2015 | Fermann | G02F 1/365 372/21 |

OTHER PUBLICATIONS

Baiz et al., "Ultrabroadband detection of a mid-IR continuum by chriped-pulse upconversion", Opt. Lett. 36, 187 (2011).
Barrett, A. et al., "Order of Dry and Wet Mixed-Length Self-Assembled Monolayers", J. Phys. Chem., 2015, 119, pp. 23943-23950.
Bartel et al., "Generation of single-cycle THz transients with high electric-field amplitudes", Opt. Lett. 30, 2805 (2005).
Ashihara, S. et al., "Spectral broadening of mid-infrared femtosecond pulses in GaAs", Optics Letters, vol. 34, No. 24, 2009, pp. 3839-3841.
Calabrese, C. et al., "Ultrafast continuum mid-infrared spectroscopy: probing the entire vibrational spectrum in a single laser shot with femtosecond time resolution", Opt. Lett. 37, 2265-2267 (2012).
Cheng et al., "Generation of tunable octave-spanning mid-infrared pulses by filamentation in gas media", Opt. Lett. 37, 1787 (2012).
Cook et al., "Intense terahertz pulses by four-wave rectification in air", Opt. Lett. 25, 1210 (2000).
Corkum, P.B. et al., "Generation of infrared supertontinuum covering 3-14 um in dielectrics and semiconductors", Optics Letters, vol. 10, No. 12, 1985, pp. 624-626.
Fuji, T. et al., "Generation of sub-two-cycle mid-infrared pulses by four-wave mixing through filamentation in air", Opt. Lett. 32, 3330 (2007).
Lanin, A.A. et al., "Multioctave, 3-18 Mm Sub-Two-Cycle Supercontinua from Self-Compressing, Self-Focusing Soliton Transients in a Solid", Opt. Lett. 2015, 40 (6), pp. 974-977.
Mouawad, O. et al., "Multioctave Midinfrared Supercontinuum Generation in Suspended-Core Chalcogenide Fibers", Opt. Lett. 2014, 39 (9), 2684-2687.
Petersen, P.B. et al., "Source for ultrafast continuum infrared and terahertz radiation", Opt. Lett. 35, 1962 (2010).
Petersen, C. R. et al., "Mid-Infrared Supercontinuum Covering the 1.4-13.3 Mm Molecular Fingerprint Region Using Ultra-High NA Chalcogenide Step-Index Fibre", Nat. Photonics 2014, 8 (11), 830-834.
Pigeon, J.J. et al., "Supercontinuum generation from 2 to 20 um in GaAs pumped by picosecond CO2 laser pulses", Optics Letters, vol. 39, No. 11, 2014, pp. 3246-3249.
Saini, T. et al., "Broadband Mid-Infrared Supercontinuum Spectra Spanning 2-15 Mm Using As2Se3 Chalcogenide Glass Triangular-Core Graded-Index Photonic Crystal Fiber", J. Light. Technol. 2015, pp. (99), 1-1.
Sanghera, J. et al., "Active and Passive Chalcogenide Glass Optical Fibers for IR Applications: A Review", J. Non. Cryst. Solids 1999, 256-257, 6-16.
Seddon, A. B., "Chalcogenide Glasses: A Review of Their Preparation, Properties and Applications", J. Non. Cryst. Solids 1995, 184, 44-50.
Shenogina, N. et al., "How Wetting and Adhesion Affect Thermal Conductance of a Range of Hydrophobic to Htydrophillic Aqueous Interfaces", PRL 102, 156101 (2009).
Stingel, A.M. et al., "Covering the vibational spectrum with microjoule mid-infrared supercontinuum pulses in nonlnear optical applications", Journal of the Optical Society of America B, vol. 34, 2017, pp. 1163-1169.
Tikhomirov, V. K., "Photoinduced Effects in Undoped and Rare-Earth Doped Chalcogenide Glasses: Review", J. Non. Cryst. Solids 1999, 256-257, 328-336.
Yu, Y. et al., "1.8-10 Mm Mid-Infrared Supercontinuum Generated in a Step-Index Chalcogenide Fiber Using Low Peak Pump Power", Opt. Lett. 2015, 40 (6), 1081-1084.
Yu, Y. et al., "A Broadband, Quasi-Continuous, Mid-Infrared Supercontinuum Generated in a Chalcogenide Glass Waveguide", Laser Photon. Rev. 2014, 8 (5), 792-798.
Yu, Y. et al., "Mid-infrared supercontinuum generation in chalcogenides," Opt. Mater. Express 3, pp. 1075-1086 (2013).
Zakery, A. et al., "Optical Properties and Applications of Chalcogenide Glasses: A Review", J. Non. Cryst. Solids 2003, 330 (1-3), 1-12.
International Search Report and Written Opinion for PCT Application No. PCT/US2016/039664, dated Sep. 30, 2016, 8 pages.

* cited by examiner

GENERATION OF HIGH ENERGY MID-INFRARED CONTINUUM LASER PULSES

PRIORITY CLAIM AND RELATED PATENT APPLICATION

This patent document is a 35 U.S.C. § 371 National Stage application of International Application No. PCT/US2006/039664 entitled "GENERATION OF HIGH ENERGY MID-INFRARED CONTINUUM LASER PULSES" and filed on Jun. 27, 2016, which claims the priority and benefits of U.S. Provisional Application No. 62/184,846 entitled "GENERATION OF HIGH ENERGY MID-INFRARED CONTINUUM LASER PULSES" and filed on Jun. 25, 2015, which are incorporated by reference in their entirety.

BACKGROUND

This patent document relates to techniques and devices that generate laser pulses in the mid-infrared (mid-IR) spectral region for optical sensing in various applications.

Light in the mid-infrared (mid-IR) spectral region including optical wavelengths of 2.5-12 µm is resonant with some fundamental transitions of molecular bond vibrations and thus can be used a sensitive probe for studying or identifying molecular structures. In various applications, mid-IR spectroscopy provides useful analytical techniques for identifying and characterizing molecules. Localized vibrations have fundamental transitions from 2.5 to 6 µm, while delocalized modes from 6 to 12 µm are sensitive probes of the overall molecular structure. Combined, the mid-IR spectrum provides a molecular fingerprint. Overtones of the fundamental modes at wavelengths shorter than 2.5 µm are sometimes studied but are often weak and difficult to interpret. Linear spectroscopies generally utilize a broadband, incoherent blackbody source to cover the entire mid-IR range. Nonlinear optical spectroscopic applications require short, high-energy (several µJ) laser pulses, but generating mid-IR pulses with wide spectral coverage and high energies simultaneously is challenging. High-energy pulses for nonlinear mid-IR spectroscopy are typically generated through nonlinear mixing of the outputs of optical parametric amplifiers (OPAs) and span only a few hundred nm. Although considered broadband, these pulses span only a small fraction of the vibrational spectrum. Nonlinear spectroscopic experiments can be performed by scanning the spectral envelope of such pulses over a wider spectral region, but this is a time consuming process and introduces additional technical difficulties, such as correcting for changes in the beam pointing and temporal overlap.

SUMMARY

This patent document disclose techniques and devices that generate supercontinuum laser pulses within a continuous mid-infrared spectral range in a suitable optical material such as chalcogenide materials and glasses in a continuous spectral range from 2.5 microns to over 10 microns for optical sensing in various applications.

Nonlinear optical spectroscopies focused on molecular vibrations require high-energy laser pulses in the mid-infrared range, e.g., laser pulses having several microjoules (µJs) per pulse. Various existing pulse generation techniques are limited to producing laser pulses of high-energies with limited spectral bandwidths or producing laser pulses of low-energies with some relatively broad spectral coverages.

It has been difficult to use various existing techniques to generate laser pulses that have high-energies and relatively continuous broad spectral ranges at the same time. The disclosed technology in this patent document can be used to meet both requirements. Tests based on the disclosed technology were performed to generate high-energy mid-IR supercontinuum laser pulses by focusing 70 fs, 30 µJ mid-IR pulses in commercially-available bulk chalcogenide glasses. The resulting supercontinuum pulses exhibit pulse energies of several µJ, sufficient for nonlinear optical applications, and remain temporally short, while spanning over two octaves from less than 2.5 µm to more than 10 µm at the 20 dB level. This facilitates capturing much of the fundamental mid-infrared vibrational transitions in a wide range of applications including nonlinear optical studies, as demonstrated with sum-frequency generation spectroscopy.

In one aspect, a method is provided for generating supercontinuum laser pulses within a continuous mid-infrared spectral range in a chalcogenide material. This method includes focusing an input laser beam of femtosecond pulses with a pulse energy higher than 10 microjoule along an optical path of the input laser beam; placing a chalcogenide material at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material; and simultaneously moving the chalcogenide material laterally relative to the input laser beam so that different portions of the chalcogenide material are exposed to the input laser beam at different times in exposing the chalcogenide material to the input laser beam in generating the supercontinuum laser pulses to avoid damage to the chalcogenide material.

In another aspect, a device is provided for optical sensing based on supercontinuum laser pulses within a continuous mid-infrared spectral range in a chalcogenide material and includes a laser source module that produces an input laser beam at an input laser wavelength of femtosecond pulses with a pulse energy higher than 10 microjoule; an input beam focusing device in an optical path of the input laser beam to focus the input laser beam at a focus location to produce a high pulse energy density; a motorized actuator that holds a chalcogenide material at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material. In this device, the motorized actuator is operable to move the chalcogenide material laterally relative to the input laser beam so that different portions of the chalcogenide material are exposed to the input laser beam at different times in exposing the chalcogenide material to the input laser beam in generating the supercontinuum laser pulses to avoid damage to the chalcogenide material. This device also includes an output beam device in an optical path of the generated supercontinuum laser pulses to direct the generated supercontinuum laser pulses as an optical sensing beam to a target for optically sensing the target.

The above and other aspects and their implementations are described in greater detail in the drawings, the description and the claims.

BRIEF DESCRIPTION OF THE DRAWINGS

FIG. 7 shows measurements for nonlinear optical application of the continuum mid-IR laser pulses in the form of sum-frequency generation spectroscopy where

DETAILED DESCRIPTION

Figure 1:
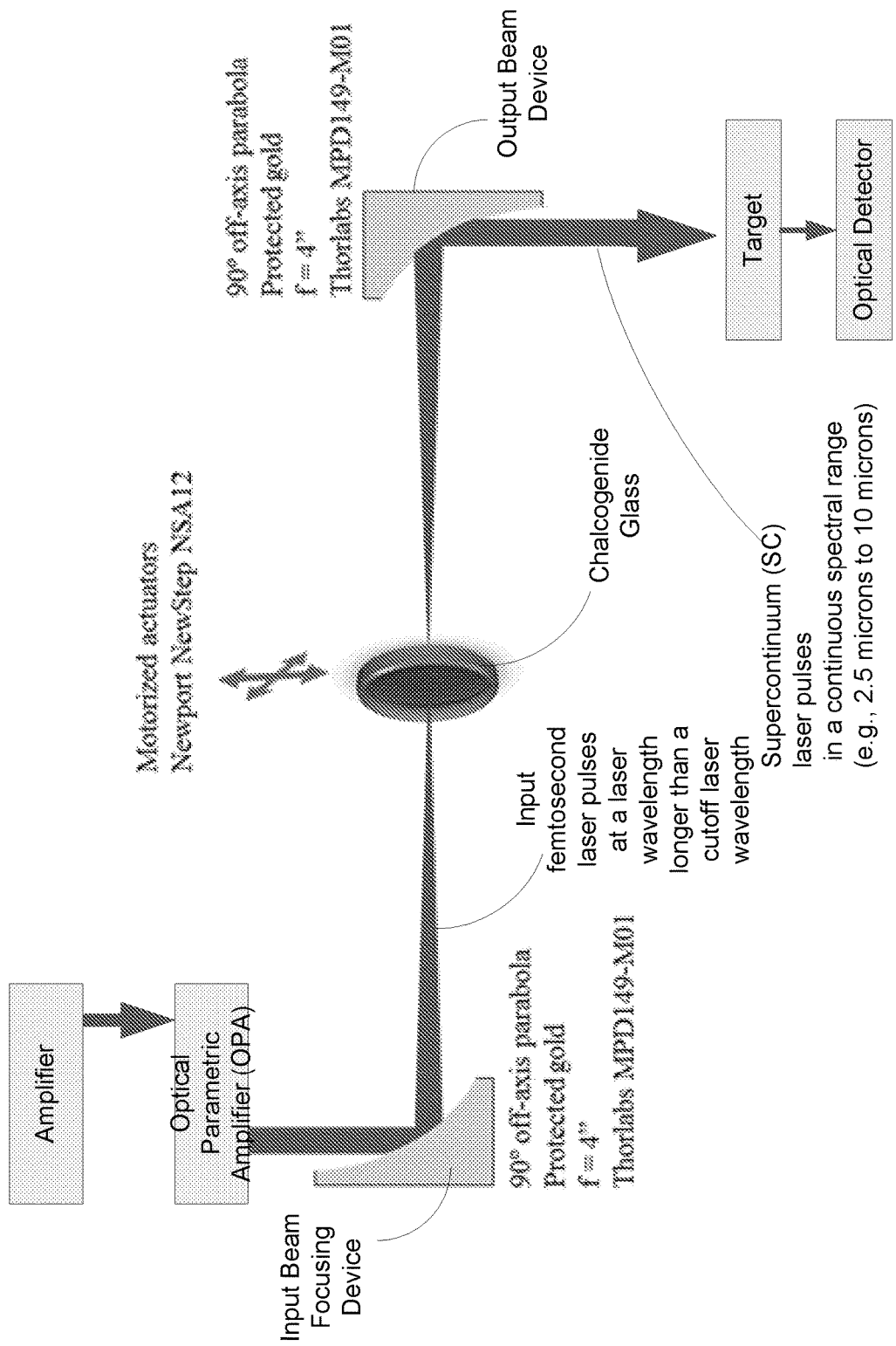
FIG. 1 shows an example of an optical sensing device in an implementation based on the disclosed technology where incident light is focused and directed into a chalcogenide glass leading to a large spectral broadening and the glass is continuously moved in the lateral two dimensions to prevent photo damage.

The disclosed technology can be used to generate light in the mid-infrared (mid-IR) spectral region (wavelengths of 2.5-20 microns corresponding to frequencies of 500-4000 $cm^{-1}$) in resonance with the vibrations of molecular bonds in identifying and characterizing molecular structures. The short wavelength range of ~2.5-7 microns (~1500-4000 $cm^{-1}$) can be used to probe specific molecular groups and the long wavelength range of ~7-12 microns (~850-1500 $cm^{-1}$) is referred to as the molecular fingerprint region and provides specific information on the overall molecular structure. Capturing both wavelength regions is important for molecular identification and analysis. Large databases have been built with mid-IR spectra forming "a library of molecular fingerprints" that can be searched for identifying and determining the molecular structure of unknown compounds. Mid-IR spectroscopy has thus become one of the cornerstone analytical methods in scientific and industrial research as well as forensic science.

The disclosed technology for supercontinuum pulse generation can be used to provide coherent optical sensing in analytical instruments for measuring vibrational spectra. The disclosed technology can be used for remote detection and nonlinear spectroscopy applications, which require coherent light sources in the mid-IR region that can be technologically difficult to achieve with other techniques. The disclosed technology can also be used to provide pulsed laser light sources to enable better detection and, depending on the pulse energy, nonlinear optical applications. The disclosed technology also further be used to provide pulsed mid-IR light sources in time-resolved vibrational spectroscopy in which the evolution of molecular structure can be followed with time-resolved mid-IR spectroscopy using pulsed IR light and molecular motions happen on the femtosecond (fs) and picosecond (ps) time-scales requiring laser pulses of this duration to capture "molecular movies".

However, generating laser pulses of fs duration in the mid-IR spectral region has been difficult with other pulse generation techniques. In some systems, fs mid-IR laser pulses are generated using optical parametric amplifiers, resulting in laser pulses that are of 40-200 fs duration and with a spectral bandwidth of 100-400 $cm^{-1}$. Although such laser pulses are referred to as "broadband" they have a spectral bandwidth that is much narrower than the vibrational spectral region from ~500 to 4000 $cm^{-1}$. This means that the vibrational spectrum has to be obtained by scanning the spectral envelope of the laser pulses over the wanted spectral region, which is a very time consuming process and also leads to technical difficulties, such as changes in the beam pointing.

Recently fs mid-IR continuum laser pulses spanning the entire vibrational frequency range (<600 to >4000 $cm^{-1}$) were generated by focusing fs light pulses of multiple colors in the near-IR through ultraviolet (UV) wavelength range in gases. While this offers a great advantage for probing the vibrational spectrum, the continuum mid-IR light pulses were only intense enough to act as probe pulses and not intense enough to act as excitation pulses in time-resolved spectroscopy and nonlinear spectroscopy. The low pulse energy also hinder propagating the laser pulses over long distances. Alternatively, spectrally wide pulses have been generated in optical fibers but these are also limited to low pulse energies. Recent developments have suggested that spectrally broad mid-IR laser pulses could be generated by propagating mid-IR laser pulses through bulk materials.

This patent document describes techniques and devices for generating high energy mid-IR continuum laser pulses, e.g., of more than 4 µJ pulse energy, by propagating high-energy fs mid-IR laser pulses in chalcogenide glasses, which are transparent in the mid-IR wavelength range (2.5-10 µm). The disclosed technology can be implemented for generating continuum mid-IR laser pulses spanning the vibrational frequency range with high pulse energy (several microjoule pulse energies) facilitating using the mid-IR continuum laser pulses as excitation pulses and in nonlinear spectroscopy and long-range pulse propagation for remote detection.

One aspect of the disclosed technology is the very high pulse energy (micro-joules) and spectral intensity of fs laser pulses which at the same time cover a very broad frequency range in the mid-IR region.

Some other pulsed laser technologies provide either a high pulse energy but very limited frequency coverage (technologies based on optical parametric amplifiers) or a wide frequency range but low pulse energies (nano-joule) with even lower spectral intensity (methods based on non-linear mixing in gases or optical fibers).

Compared to some other pulse generation methods based on non-linear mixing in gases, the disclosed technology provides, among other advantages, more than an order of magnitude higher overall pulse energy. In other pulse generation techniques, the most of the energy tends to be at low frequencies. The disclosed technology can be used to provide about 3 orders of magnitude higher spectral intensity (intensity per frequency unit) in the mid-IR frequency range than other methods. Conducted tests demonstrate such performance by using a md-IR array detector registering the same number of counts using our new method with a neutral density filter with an optical density of 3 as in other pulse generation techniques without a neutral density filter.

The disclosed technology in this document, in some implementations, involves propagating intense mid-IR laser pulses through IR-transparent materials. In conducted tests, chalcogenide glasses were used to demonstrate the disclosed technology and other IR-transparent materials may also be used for implementing the disclosed technology. In conducted tests, the incident mid-IR pulses were of femtosecond pulse duration containing a spectral bandwidth of ~300 $cm^{-1}$ with a pulse energy of tens of micro-joules, and the pulses were generated through nonlinear mixing of the output pulses from an optical parametric amplifier (OPA). The disclosed technology can be implemented with various laser sources to generate the fs pulses different from the specific OPA design used in our tests.

FIG. 1 shows an example of an optical sensing device in an implementation based on the disclosed technology for optical sensing based on supercontinuum laser pulses within a continuous mid-infrared spectral range generated in a chalcogenide material. In this example, the device includes a laser source module that produces an input laser beam at an input laser wavelength of femtosecond pulses with a pulse energy higher than 10 microjoule. Specifically, the illustrated laser source module includes a laser (not shown), an optical amplifier and an OPA. This device includes an input beam focusing device, e.g., a parabola reflector or a lens, in an optical path of the input laser beam to focus the input laser beam at a focus location to produce a high pulse energy density. The chalcogenide material is held by a motorized actuator at a selected location along the optical path of the laser beam so that the laser intensity at the chalcogenide material is sufficiently high to cause nonlinear optical absorption in the chalcogenide material that causes conversion of input optical energy into supercontinuum laser pulses of a pulse energy at or above a microjoule level at optical wavelengths within a broad continuous mid-infrared spectral range without damaging the chalcogenide material. In this device, the motorized actuator is operable to move the chalcogenide material laterally relative to the input laser beam so that different portions of the chalcogenide material are exposed to the input laser beam at different times in exposing the chalcogenide material to the input laser beam in generating the supercontinuum laser pulses to avoid damage to the chalcogenide material. This device also includes an output beam device, e.g., a parabola reflector, in an optical path of the generated supercontinuum laser pulses to direct the generated supercontinuum laser pulses as an optical sensing beam to a target for optically sensing the target. An optical detector can be provided to detect light out of the target illuminated by the generated supercontinuum laser pulses (e.g., optical transmission of the target) to perform desired optical sensing of the target. The target can be a gas material, a liquid or a solid material depending on sensing applications.

In FIG. 1, both the input and output optical devices are focused by and re-collimated by using off-axis parabolas but other optical devices may also be used. For example, suitably designed optical lenses could potentially also be used. For the input optical device that focuses the input laser beam onto the chalcogenide glass, an optical lens can be used to provide the desired focusing operation. For the output optical device, the wide spectral range of the supercontinuum pulses generated from the chalcogenide glass provide technical challenges in the lens design due to the optical dispersions and distortions/aberrations at different optical wavelengths over the wide continuum spectrum. The IR-transparent chalcogenide glass material is placed in the optical path near the focus of the incident pulses. Propagating the incident laser pulses through the material leads to great broadening of the pulse spectrum due to nonlinear optical processes. A loss of overall pulse energy is observed by propagating the incident laser pulses through the material. A tradeoff between exiting pulse energy and spectral bandwidth is observed. When the IR-transparent material is closer to the focus a greater spectral broadening occur but also a higher loss of pulse energy compared to when the IR-transparent material is further away from the focus. This provides some tunability in the spectral coverage versus pulse energy that can be tailored to the given application. When the IR-transparent material is close to the focus, optical damage to the material occur. To prevent this damage the material is moved in the two lateral dimensions using motorized actuators.

Figure 2:
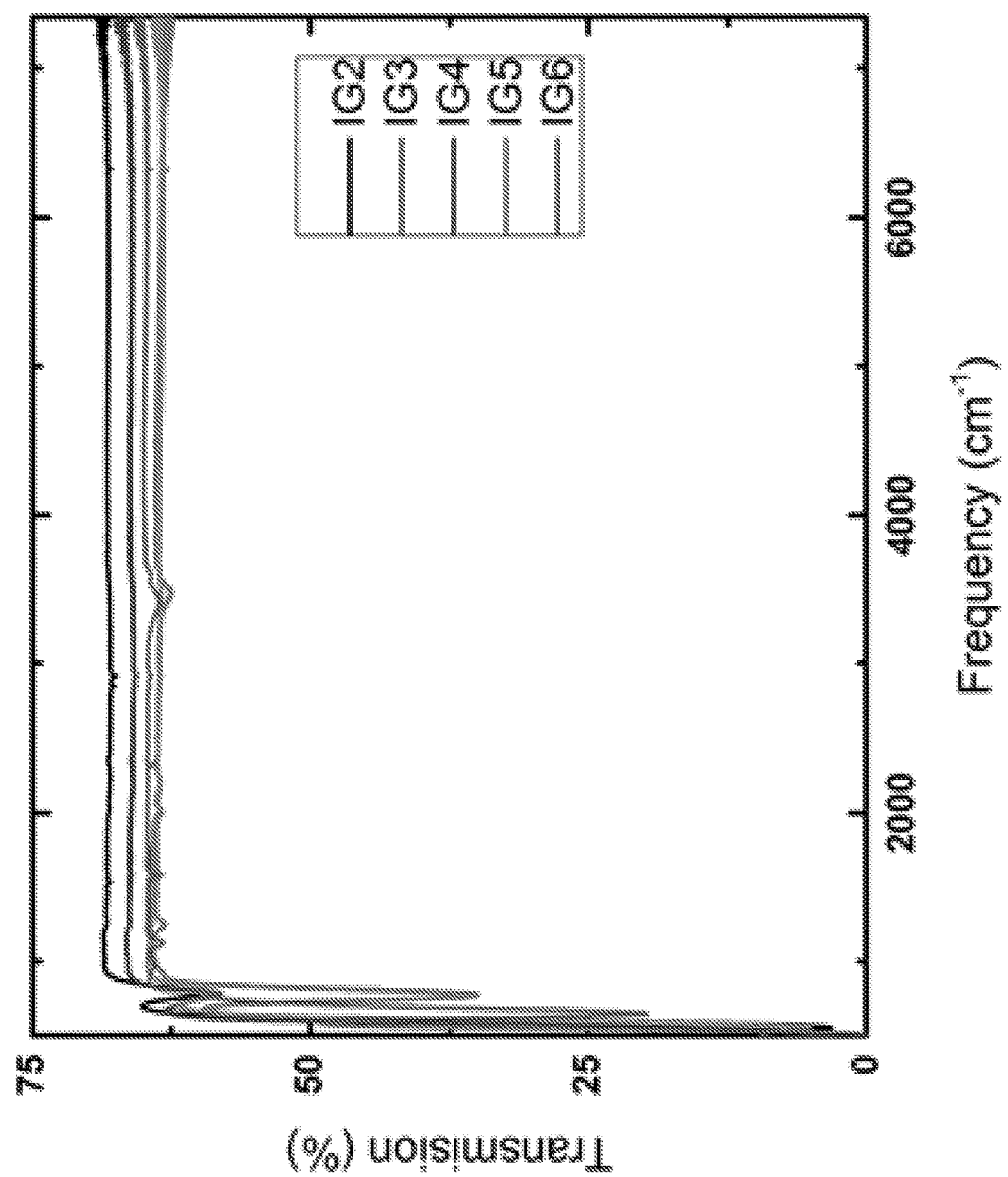
FIG. 2 shows examples of the optical transmission spectra of examples of chalcogenide glasses suitable for implementing the disclosed technology.

Experiments were conducted to teste five different chalcogenide glasses (IG2, IG3, IG4, IG5, and IG6) acquired from Naked Optics. The thickness of the materials were 2 mm and the diameter of the windows were 1 inch. The composition of the chalcogenide glasses are $Ge_{22}As_{12}Se_{55}$ (IG2), $Ge_{30}As_{13}Se_{32}Te_{25}$ (IG3), $Ge_{10}As_{40}Se_{50}$ (IG4), $Ge_{28}Sb_{12}Se_{60}$ (IG5), and $As_{40}Se_{60}$ (IG6), respectively. The composition of the IG2 glass as provided by the manufacture was labeled as $Ge_{22}As_{12}Se_{55}$ but the correct composition might be $Ge_{32}As_{12}Se_{55}$. Their transmission spectra in the mid-IR range is shown in FIG. 2. Tests were conducted to study the glass dependence, incident wavelength dependence, and incident intensity dependence of the generated pulse spectra. The overall pulse energy of the incident pulses were kept at 30 µJ and gold coated 4" focal length 90 degree off-axis parabolas were used to focus the incident light and re-collimate the exciting beam.

Propagation of the light through the material leads to a large broadening of the pulse spectrum. The generated pulse spectra are so wide that is it difficult to measure the pulse spectra reliably. In our study we have used a mercury-cadmium-telluride (MCT) array detector (IR Associates/IR Systems) with an IR monochromator (Horiba), where the MCT detector elements are doped for highest response at 10000 nm light giving an overall detection range of 2000-12000 nm. A large limitation on measuring the spectra is the efficiencies of the gratings in the monochromator. Two gratings were used to measure the spectra: 58 grooves/mm blazed at 3600 nm and 30 grooves/mm blazed at 8000 nm. The generated pulse spectra are broadest when the material is near the focus of the incident laser pulses.

Figure 3:
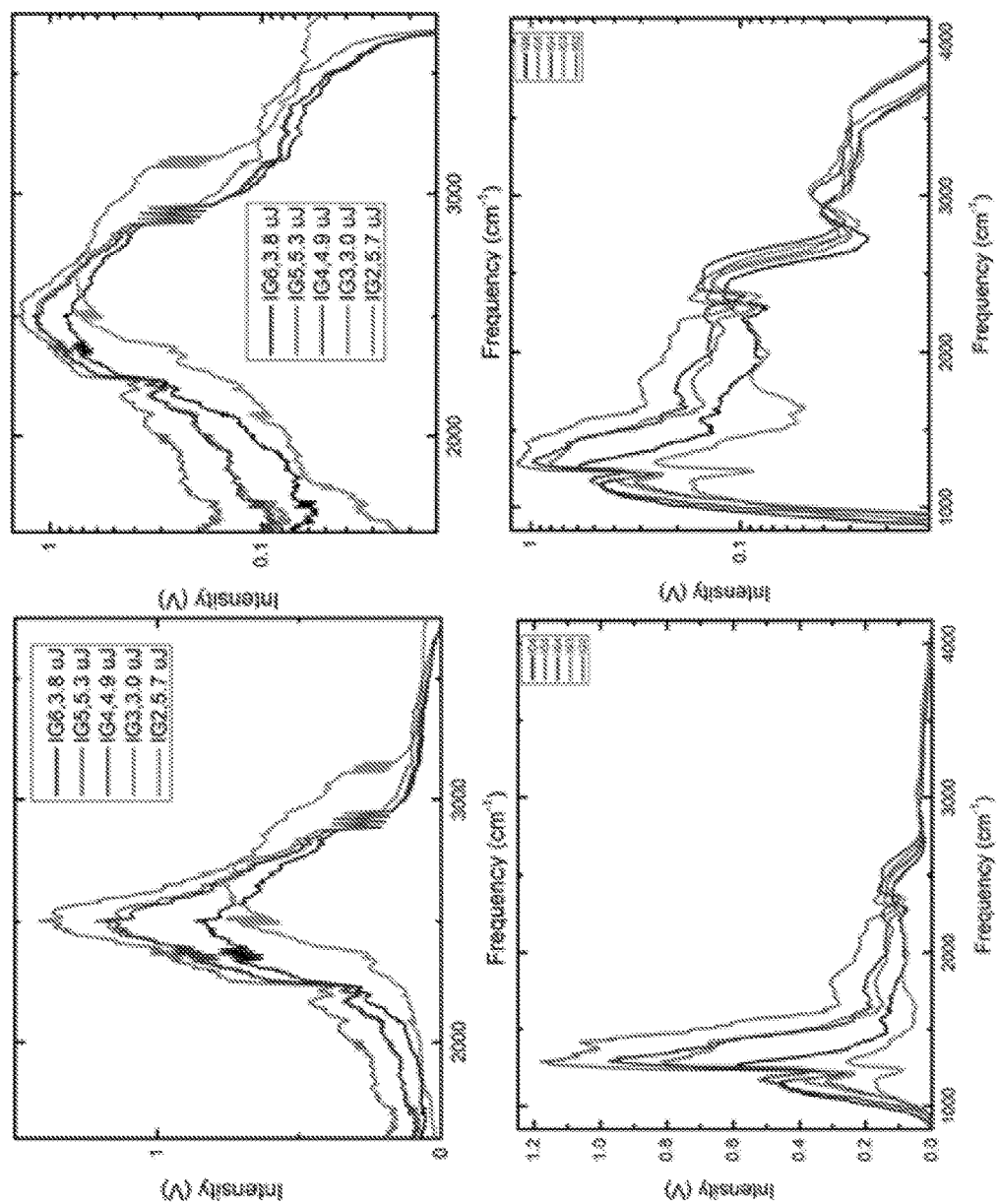
FIG. 3 includes four charts of optical signal intensity measurements as a function of optical frequency to show the dependence of the generated optical spectra of five tested chalcogenide glasses, where the generated pulse spectra with propagation of pulses are centered at or near 3800 nm through the different chalcogenide glasses with the material close to the focus of the incident pulses. The spectra measured on the two different gratings are shown on the top and bottom, respectively, and on linear (left) and logarithmic (right) scales. The legend lists the pulse energies.

FIG. 3 shows the generated pulse spectra measured on two different gratings for the 5 different chalcogenide glasses. As the figure illustrates the generated laser pulses cover the spectral range from 2500 to 10000 nm or 1000 to 4000 cm-1 and thus most of the relevant vibrational frequency range.

Figure 4:
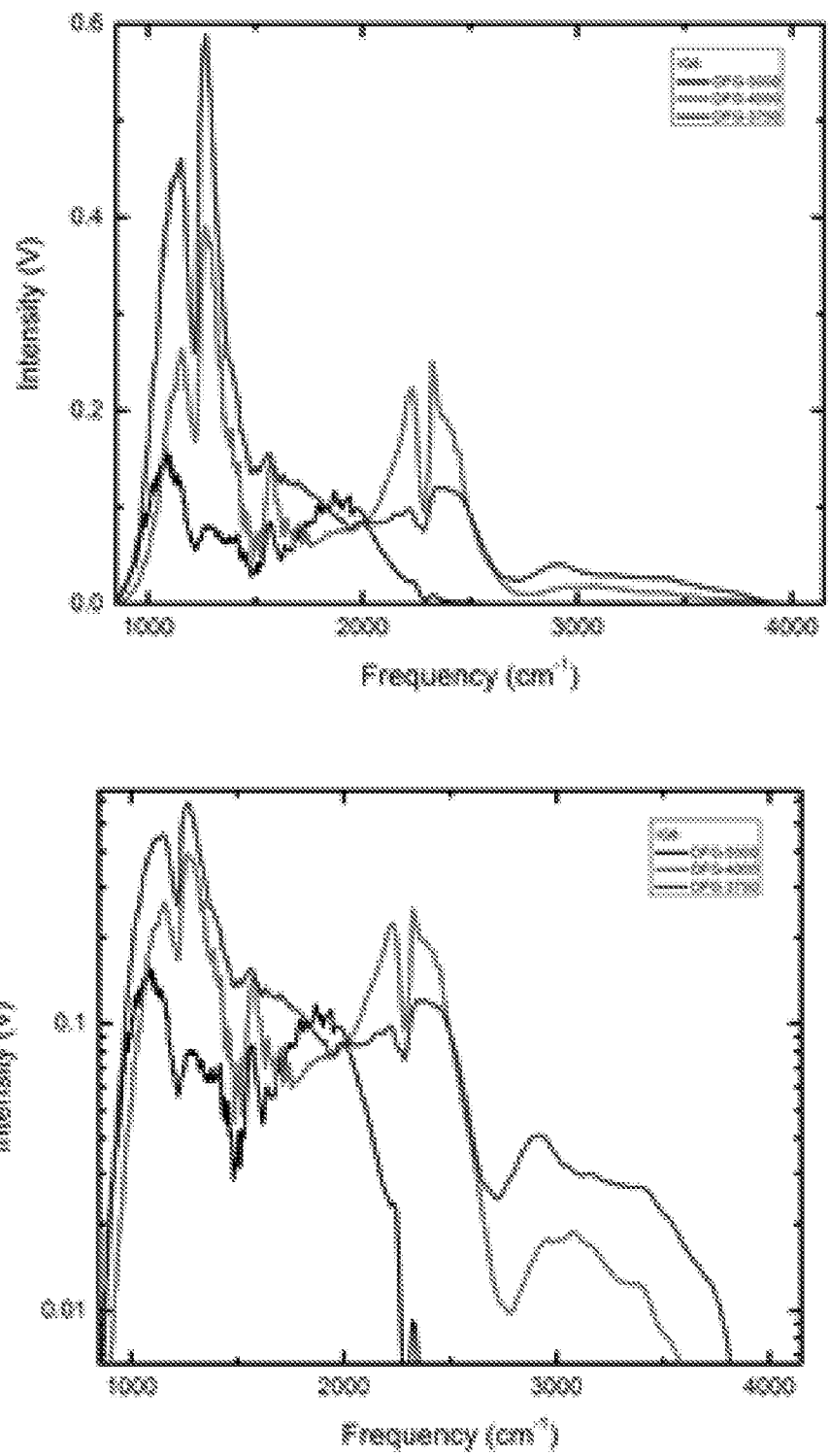
FIG. 4 shows examples of measurements showing the dependence of the incident optical wavelength in continuum generation in the glass material IG6.

The generated pulse spectra depend greatly on the wavelength of the incident laser pulses. FIG. 4 shows the generated pulse spectra in IG6 using incident wavelengths of 3800 nm, 4000 nm, and 5000 nm. Using incident laser pulses of shorter wavelengths leads to rapid photodamage of the material that cannot be prevented by translating the material in the lateral dimensions.

Figure 5:
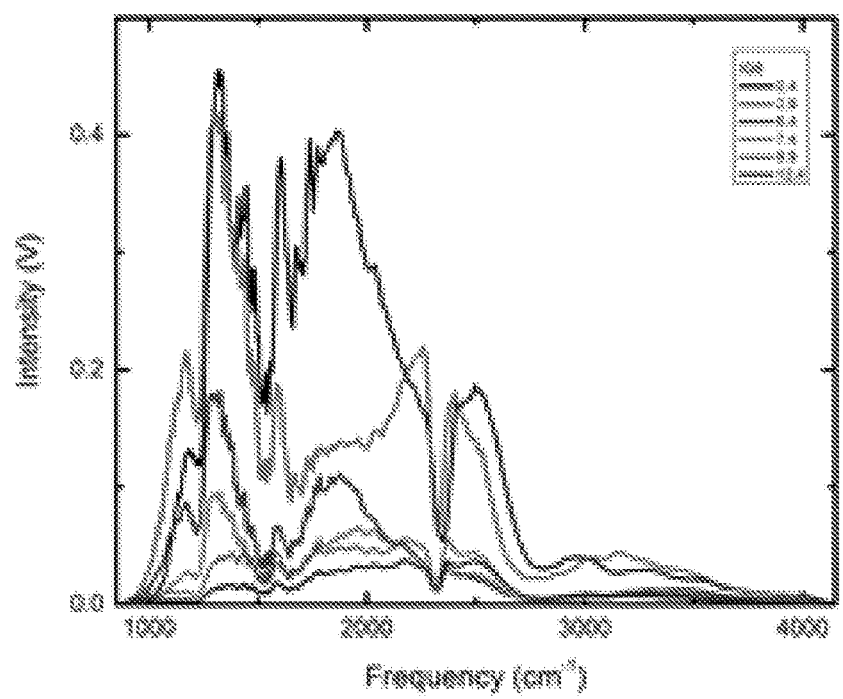
FIG. 5 shows the measured dependence of continuum generation in IG6 on the incident laser pulse intensity.
Figure 5:
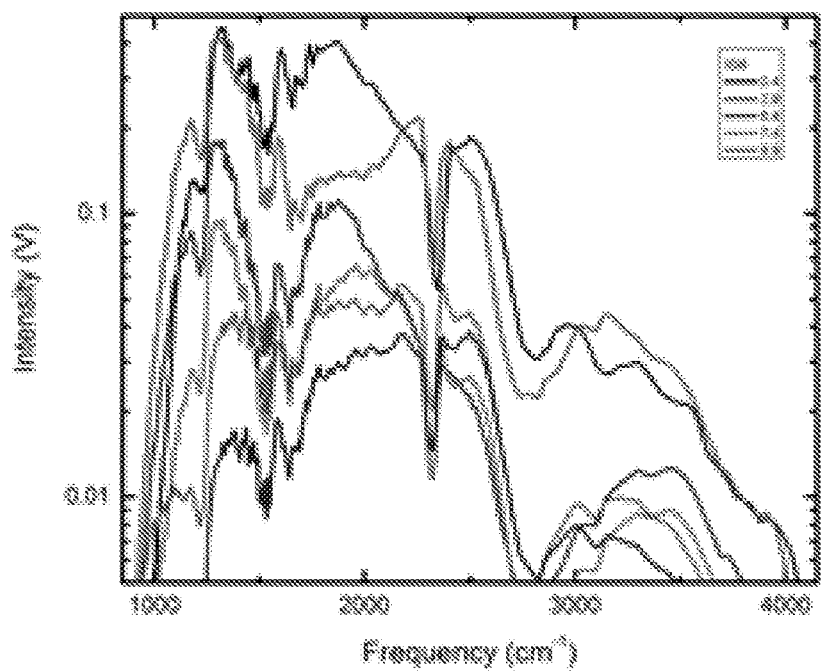

The generated pulse spectra also depend on the energy density of the incident light, which we vary by changing the position of the material with respect to the focus of the incident laser pulses. This dependence is shown in FIG. 5.

The pulse energies when the material is near the focus of the incident laser pulses is about 10% of the incident pulse energies. As the material is moved further away from the focus resulting in a narrower pulse spectrum, the pulse energy increases to about half the incident pulse energy mostly due to the reflection loss at normal incidence. Putting the material at Brewster's angle will minimize the reflection loss and increase the pulse energy with the additional complexity of having to move the material in two dimensions without translating the material along the beam propagation direction. Alternatively antireflecting coatings could be used to reduce the reflection loss and increase the pulse energy of the generated continuum pulse. For the case IG3 close to the focus of the incident pulses, which produced the widest pulse spectrum, we obtain a pulse energy of 4 micro joule, which is strong enough for nonlinear optical applications and long-range pulse propagation. With the glass positioned further away from the focus, higher pulse energies are obtained but with narrower spectral bandwidths.

Figure 6:
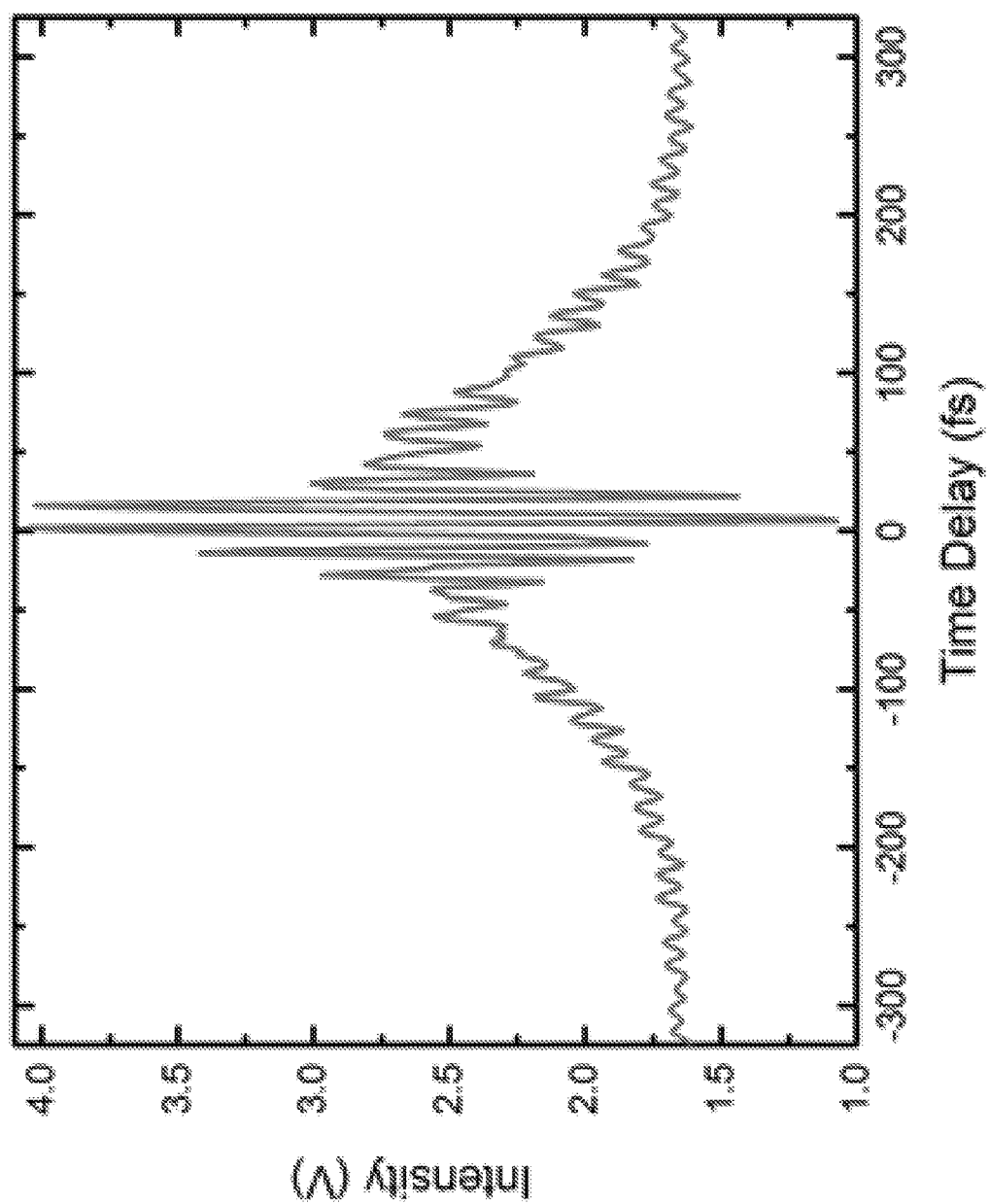
FIG. 6 shows the temporal characterization of the generated supercontinuum pulses by the second order autocorrelation in a 0.3 mm-thick GaSe crystal illustrating that the generated pulses are temporally short.

The pulse duration is lengthened by propagation through the chalcogenide material. The pulses can be compressed by propagating the pulses though other materials, using optical prisms, or a pulse shaper. FIG. 6 shows the second order autocorrelations in a 0.3 mm thick GaSe of the generated pulses illustrating that the pulses are temporally short.

After characterizing the generated laser pulses, a multiplex sum-frequency generation (SFG) was conducted to illustrate the application of such supercontinuum laser pulses in nonlinear optical spectroscopy. The SFG is a second-order nonlinear optical technique in which the mid-IR continuum pulse excites the sample and is mixed with a narrowband visible or near-IR laser pulse (in our case a 10 $cm^{-1}$ wide pulse centered at 794 nm) giving rise to a second-order response at the sum of the incident frequencies.

Figure 7A:
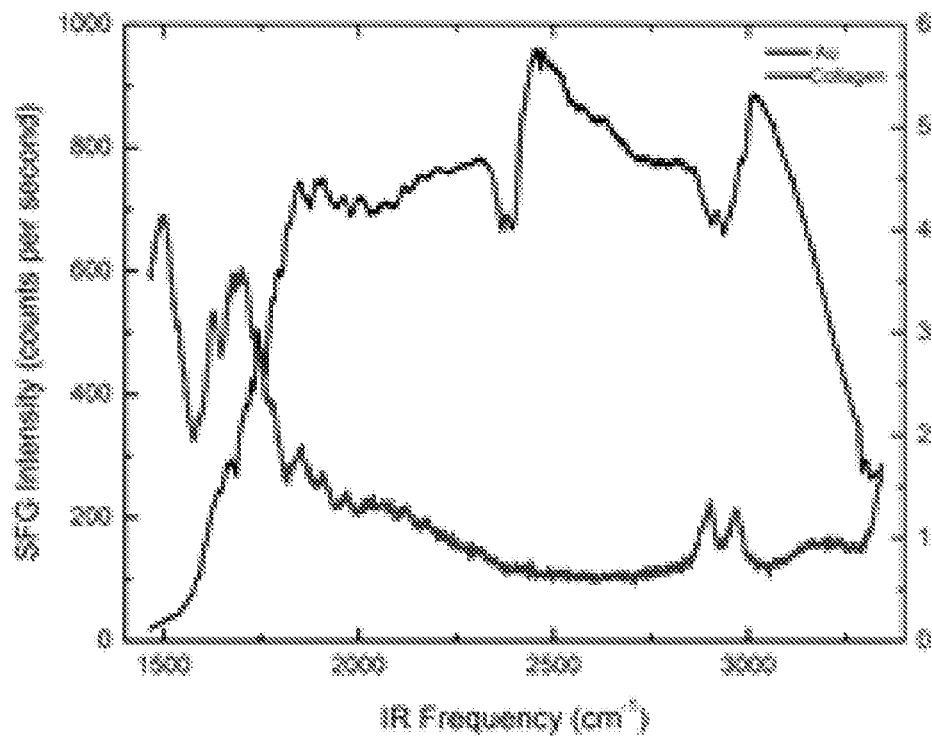
FIG. 7A and FIG. 7B show the SFG spectra of a non-resonant sample (gold) and a resonant sample (collagen) in the SSP polarization combination (FIG. 7A) and PPP polarization combination (FIG. 7B) for the SFG signal, visible, and IR light.
Figure 7B:
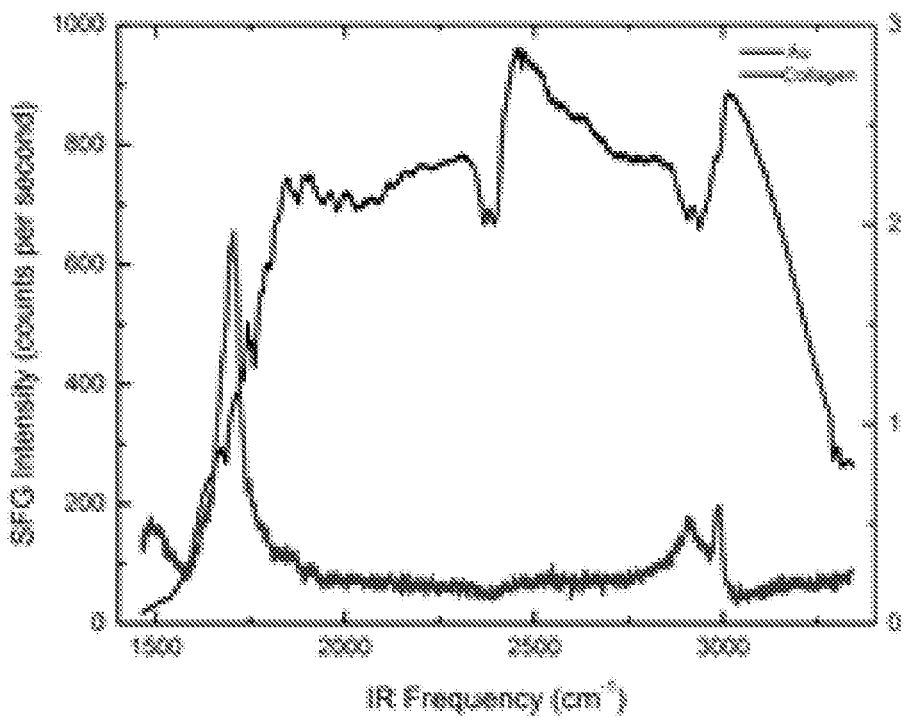

FIG. 7 includes FIGS. 7A and 7B and shows measurements of the SFG spectrum at the resulting IR frequency of both a non-resonant gold sample and a resonant sample of collagen on $CaF_2$. The SFG signal was measured on a Spec-10 CCD camera (Princeton Instruments) and the SFG spectra were acquired as 10 averages of 5 second exposures for the gold samples and 20 averages of 60 second exposures for the collagen sample. This illustrates that the generated laser pulses are of high enough energy to be used in nonlinear optical methods such as SFG and 2D-IR spectroscopy.

In a recent testing of the disclosed technology, mid-IR laser pulses, generated by nonlinear mixing of the output of an OPA, were focused through chalcogenide glasses. Various other materials and components may be used to implement the disclosed technology, including use of other IR-transparent materials, other incident wavelengths, other light sources of the incident light, and/or other focusing optics.

The reflection loss could also be minimized by using anti-reflecting coatings or putting the material at Brewster's angle. The short frequency cutoff of the generated spectrum is limited by the transmission of the chalcogenide glasses. Other IR-transparent materials could lead to a higher conversion efficiency with lower energy loss or a different spectral coverage of the exciting pulses. Other IR-transparent materials could also facilitate using near-IR or even visible light to generate the continuum mid-IR laser pulses. This would be advantageous since higher energy pulses can be made at near-IR and visible wavelengths potentially leading to higher pulse energies in the mid-IR range of the exciting pulses.

The higher pulse energy of the spectrally wide pulses in the mid-IR frequency range generated from the disclosed technology may be used to facilitate several applications. These include the use of the pulses in nonlinear optical applications and remote detection facilitated by long-range propagation of the laser pulses.

Referring to FIG. 1, in our conducted tests, a commercial OPA (Coherent OPerA Solo) is pumped by 1 kHz, 3.3 W, 25 fs, 800 nm pulses from a regenerative Ti:sapphire amplifier (Coherent Legend Elite Duo). Mid-IR pulses with a spectral bandwidth around 300 cm-1, pulse energy of 30 µJ, and pulse duration of approximately 70 fs are generated by non-collinear DFG mixing of the OPA output. These mid-IR pulses, with a beam diameter of about 4 mm, are focused through a chalcogenide window and re-collimated using off-axis parabolic mirrors (f=4", protected gold) with the chalcogenide placed in the optical path near the focus of the incident pulses. To prevent optical damage, the glass is continuously moved in the two lateral dimensions using motorized actuators. The generated pulses were dispersed in an IR monochromator (Horiba) with a grating blazed at 8 µm (30 grooves/mm) onto a mercury-cadmium-telluride (MCT) array detector (IR Associates/IR Systems). The MCT detector elements are doped for highest response at 10 µm, giving an overall detection range of 2-12 µm. All measured spectra were normalized to the grating and detector efficiency curves. The monochromator is equipped with order-sorting filters from 2.44 µm to 13 µm.

Given the input laser pulse energy density, the glass sample was placed at various locations relative to the laser focus location. Table 1 below shows measurements of pulse energies (µJ) of supercontinuum pulses generated in the five chalcogenide glasses at positions relative to focus of the incident beam.

| Position | IG2 | IG3 | IG4 | IG5 | IG6 |
| --- | --- | --- | --- | --- | --- |
| −6.0 mm | 9.6 | — | — | — | 6.2 |
| −3.5 mm | 5.7 | 3.0 | 4.9 | 5.3 | 3.8 |
| 0.0 mm | 3.9 | 1.9 | 3.0 | — | 2.2 |
| +1.0 mm | 4.1 | — | — | — | 2.7 |
| +3.5 mm | 6.3 | 3.1 | 5.1 | 5.5 | 4.2 |
| +6.0 mm | 7.0 | — | — | — | 4.6 |

Figure 8:
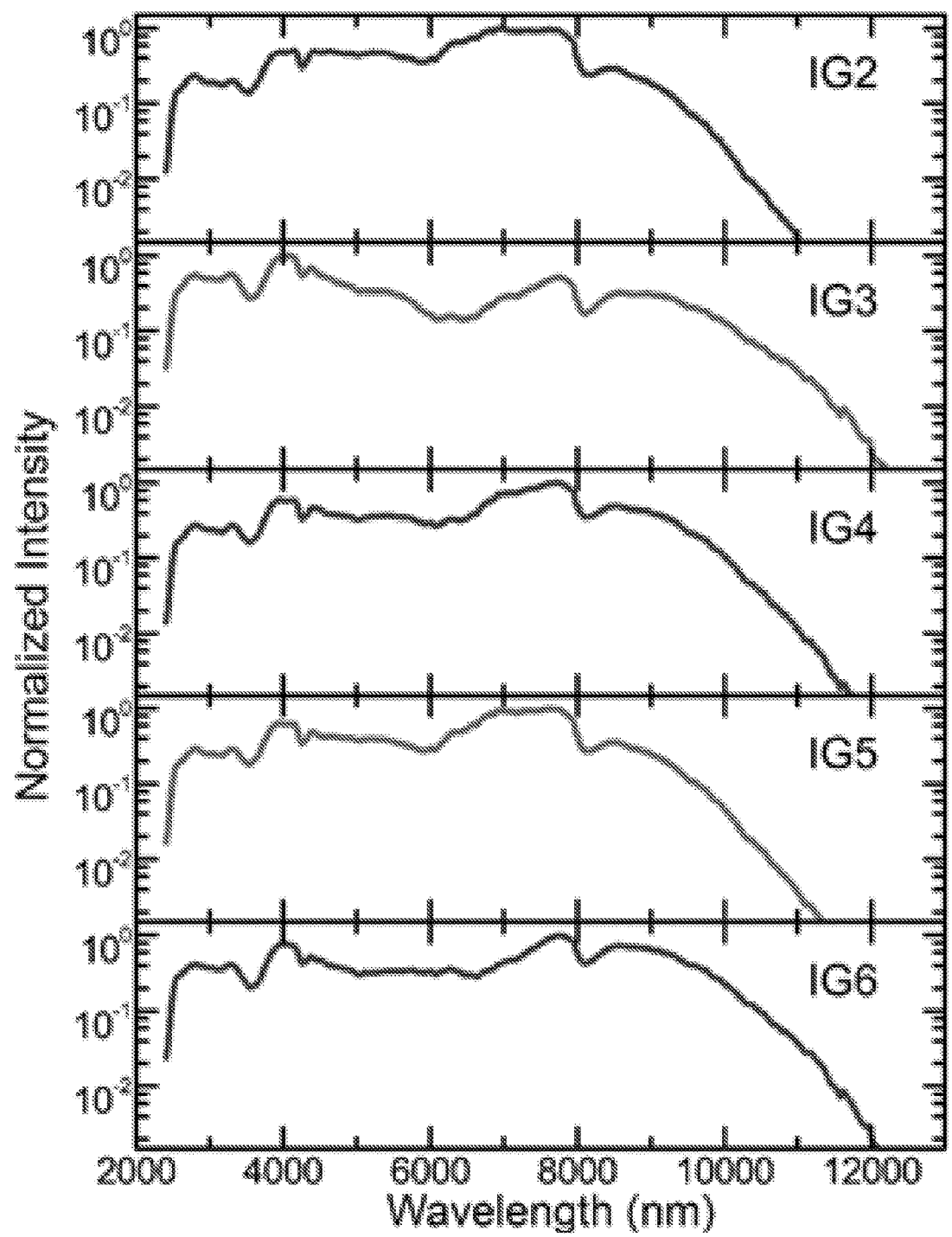
FIG. 8 shows measurements of spectra of mid-infrared supercontinuum generated in the chalcogenide glasses, measured with glasses located 3.5 mm in front of the focus of the 30 µJ, 3750 nm incident pulse.

FIG. 8 includes five measurements for spectra of mid-infrared supercontinuum generated in the chalcogenide glasses, measured with glasses located 3.5 mm in front of the focus of the 30 µJ, 3750 nm incident pulse.

For all experiments, the incident pulse energy was held at 30 µJ, corresponding to a peak power of ~430 MW. At a distance of 3.5 mm from the focus, the beam spot is approximately 425 µm, corresponding to an energy density of ~300 $GW/cm^2$. As shown by the measurements in FIG. 8, the generated laser pulses cover the spectral range from <2.5 to 11 μm at about the 20 dB level. At the 10% level, which is more relevant to spectroscopic applications, the bandwidth is 2.5 to 10 μm, corresponding to 1000 to 4000 cm$^{-1}$, covering most of the fundamental vibrational frequency range including the fingerprint region. The supercontinua generated in the different glasses are qualitatively very similar. The sharp cutoff at short wavelengths is caused by the 2440 nm order sorting filter in the monochromator. The overall pulse energy is significantly reduced after propagation through the chalcogenide glass due to multiphoton absorption, which can also lead to photodamage. IG2 and IG6 were chosen for further study. The energy of the supercontinuum generated in IG2 is highest of the five glasses, while IG6 produces the broadest spectrum without burning. IG3 has the broadest spectrum but a lower damage threshold and produces lower energy supercontinuum pulses.

Figure 9:
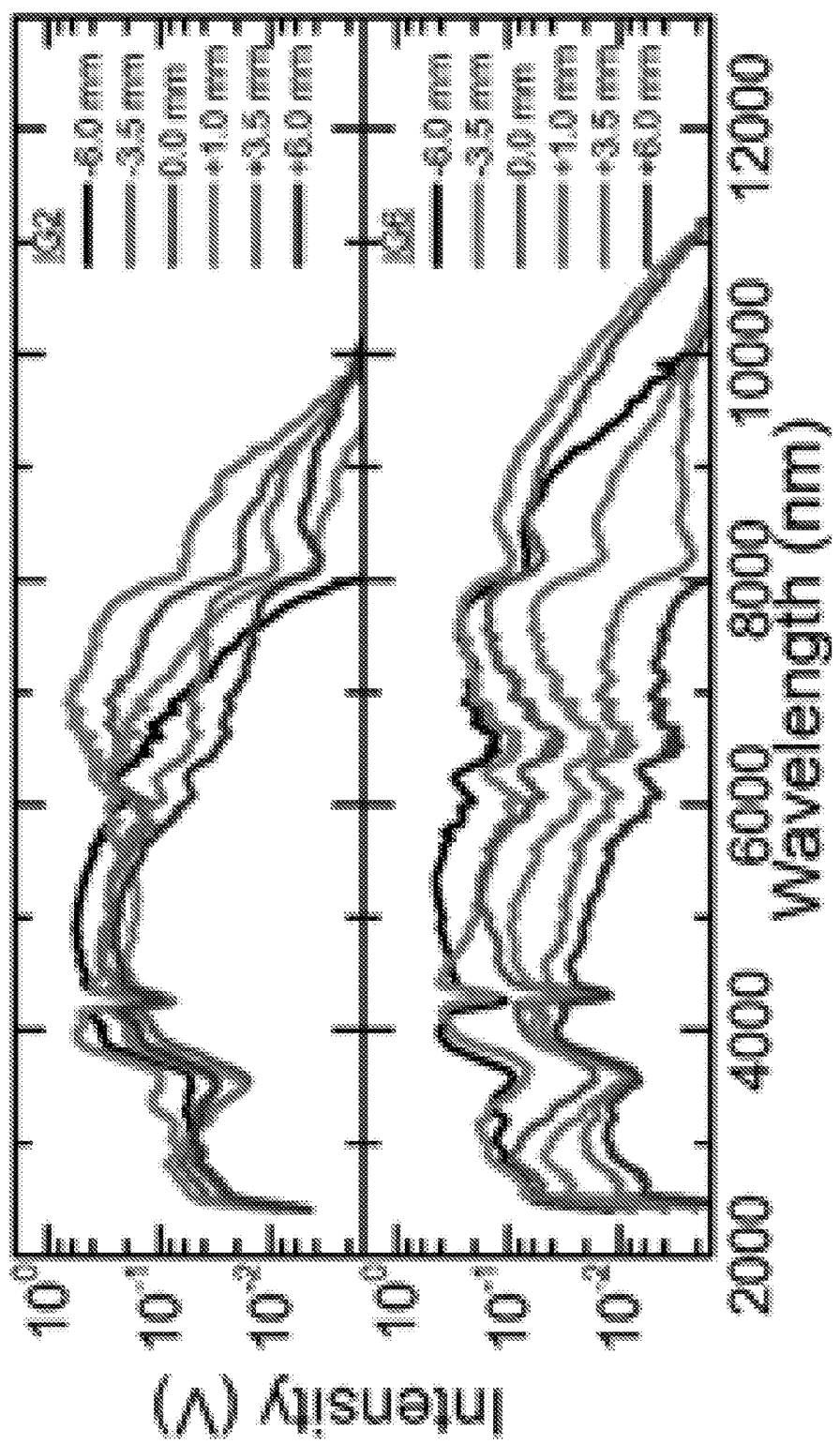
FIG. 9 shows measurements of supercontinua generated in IG2 (top) and IG6 (bottom) as a function of glass position with an incident 30 µJ, 3750 nm pulse.

The generated pulse spectra depend on the energy density of the incident light, which we control by changing the position of the material with respect to the focus of the incident laser pulses. As the IR-transparent material is moved closer to the focus of the incident beam, greater spectral broadening and decreased pulse energy is observed. This provides some flexibility in the spectral coverage versus pulse energy that can be tailored to a given application. The pulse energies as the glass is varied from 6 mm in front of to 6 mm behind the focus are listed in Table 1 and the associated spectra for IG2 and IG6 are shown in FIG. 9

When the material is near the focus of the incident beam, the transmitted supercontinuum pulse energies are around 10%. As the material is moved farther away from the focus, resulting in a narrower spectrum, the pulse energy increases to about half of the incident energy. The loss far from the focus is mostly due to reflection loss at normal incidence. Putting the material at Brewster's angle should minimize the reflection loss and increase the pulse energy but has the additional complexity of having to move the material in two dimensions without translating the material along the beam propagation direction. Anti-reflection coatings can decrease the reflection loss and increase the energy of the broadened pulse, but at high intensities the nonlinear absorption loss remains significant. With the focus at the optical surface of the material, damage occurs despite lateral translation of the sample. For IG2 and IG6, positioning the glass 3.5 mm in front of the focus of the incident light produced the widest pulse spectrum without damaging the windows. The pulse energies obtained here were 5.7 and 3.8 μJ, respectively, which are strong enough for nonlinear optical applications.

Figure 10:
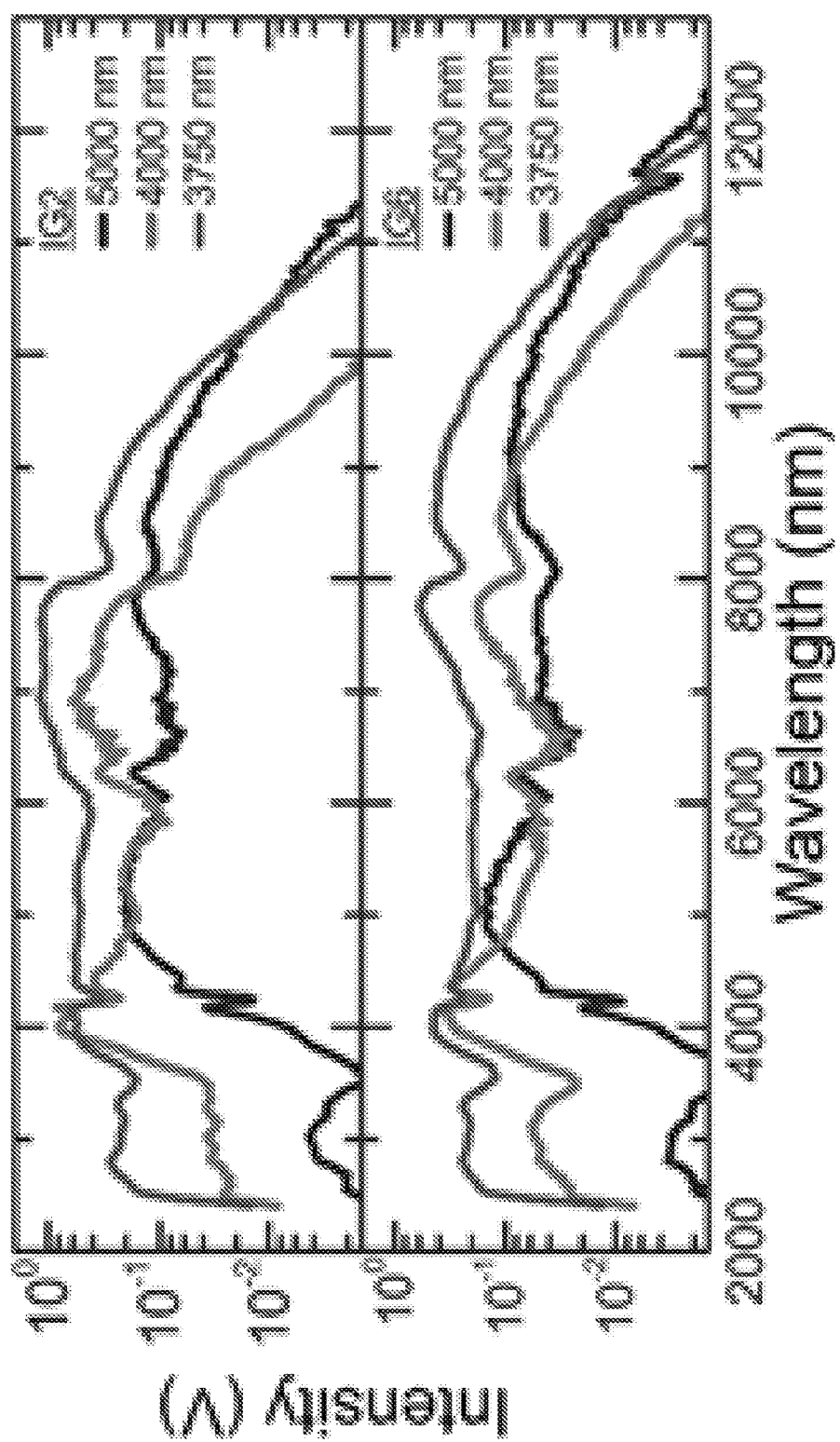
FIG. 10 shows the supercontinua generated in IG2 and IG6 with incident wavelengths of 3750 nm, 4000 nm, and 5000 nm, demonstrating that the generated pulse spectrum depends greatly on the wavelength of the incident laser pulses.

The generated pulse spectrum depends greatly on the wavelength of the incident laser pulses. FIG. 10 shows the supercontinua generated in IG2 and IG6 with incident wavelengths of 3750 nm, 4000 nm, and 5000 nm. Using shorter wavelengths leads to rapid photodamage that cannot be prevented by lateral translation of the material. Increasing the input wavelength results in less broadening to shorter wavelengths, but higher output energy of the supercontinuum pulse.

In the conducted tests for generating supercontinuum laser pulses, the optical wavelength of the incident femtosecond laser pulses should be set a wavelength longer than a threshold cutoff wavelength where the optical absorption at the cutoff wavelength or shorter wavelengths becomes significantly large that would undesirably damage the glass material and such damage is permanent. For the tested chalcogenide glass material, this cutoff wavelength is below 3725 nm. For incident optical wavelengths longer than this cutoff wavelength, the significant nonlinear optical absorption for the desired nonlinear optical generation of the supercontinuum laser pulses may still lead to optical damage to the glass material for extended exposure. Based on conducted tests, the glass material should constantly moved in time during the pulse generation to avoid such damage.

Therefore, to operate the device in FIG. 1, the input laser beam of femtosecond pulses with a pulse energy higher than 10 microjoule is focused along an optical path of the input laser beam and the chalcogenide material is at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material. The motorized actuator is used to simultaneously move the chalcogenide material laterally along two directions relative to the input laser beam so that different portions of the chalcogenide material are exposed to the input laser beam at different times in exposing the chalcogenide material to the input laser beam in generating the supercontinuum laser pulses to avoid damage to the chalcogenide material. The motorized actuator used in tests included two linear stages that each were moved at constant speed back and forth between two point, e.g., a 5-10 mm distance. The two stages were moved at different speeds so they created an offset diamond pattern filling out a box of about 10 by 10 mm over time but without repeating the same trace consecutively. The speeds the two linear stages were moved at was approximately 1 and 2 mm/s, respectively.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for generating supercontinuum laser pulses within a continuous mid-infrared spectral range in a chalcogenide material, comprising:

focusing an input laser beam of femtosecond pulses with a pulse energy higher than 10 microjoule along an optical path of the input laser beam;

placing a chalcogenide material at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material; and simultaneously moving the chalcogenide material laterally relative to the input laser beam so that different portions of the chalcogenide material are exposed to the input laser beam at different times in exposing the chalcogenide material to the input laser beam in generating the supercontinuum laser pulses to avoid damage to the chalcogenide material.

2. The method as in claim 1, wherein:
the chalcogenide material is a chalcogenide material glass.

3. The method as in claim 2, wherein:
the chalcogenide glass material includes Ge and As.

4. The method as in claim 2, wherein:
the chalcogenide material is a glass material that includes Ge and Se.

5. The method as in claim 2, wherein:
the chalcogenide material is a glass material that includes As and Se.

6. The method as in claim 2, wherein:
the chalcogenide glass material includes Ge, As, Se, Sb or Te.

7. The method as in claim 2, wherein:
the chalcogenide glass material includes $Ge_{33}As_{12}Se_{55}$, $Ge_{30}As_{13}Se_{32}Te_{25}$, $Ge_{10}As_{40}Se_{50}$, $Ge_{28}Sb_{12}Se_{60}$, or $As_{40}Se_{60}$.

8. The method as in claim 1, wherein:
each laser pulse of the input laser beam has a pulse energy density greater than 100 $GW/cm^2$ and an input pulse energy of more than 10 microjoules.

9. The method as in claim 8, wherein:
the chalcogenide material is placed at a location away from a focus of the laser beam along the optical path.

10. The method as in claim 8, wherein:
the input laser beam is controlled at a laser wavelength greater than a cutoff laser wavelength that is shorter than 3800 nm, wherein input light at a laser wavelength shorter than the cutoff laser wavelength strongly absorbed to cause damage to the chalcogenide material.

11. The method as in claim 10, wherein:
the input laser beam is controlled at a laser wavelength greater than a cutoff laser wavelength that is shorter than 3725 nm to avoid damage to the chalcogenide material caused by a high optical energy density of each laser pulse of the input laser beam.

12. The method as in claim 11, wherein:
the input laser beam is controlled at a laser wavelength around 3725 nm.

13. The method as in claim 11, wherein:
the input laser beam is controlled at a laser wavelength longer than 3725 nm.

14. The method as in claim 11, wherein:
the input laser beam is controlled at a laser wavelength around 3725 nm.

15. The method as in claim 10, wherein:
the input laser beam is at or near 4000 nm.

16. The method as in claim 10, wherein:
the input laser beam is at or near 5000 nm.

17. The method as in claim 1, wherein:
setting the energy of each laser pulse of the input laser beam at tens of microjoules when incident at the chalcogenide material; and controlling an optical wavelength and each pulse energy density of the input laser beam generate the supercontinuum laser pulses at or above a 20 dB level in a continuous spectral range from about 2.5 microns to about 10 microns in wavelength.

18. A device for optical sensing based on supercontinuum laser pulses within a continuous mid-infrared spectral range in a chalcogenide material, comprising:

a laser source module that produces an input laser beam at an input laser wavelength of femtosecond pulses with a pulse energy higher than 10 microjoule;

an input beam focusing device in an optical path of the input laser beam to focus the input laser beam at a focus location to produce a high pulse energy density;

a motorized actuator that holds a chalcogenide material at a selected location along the optical path of the laser beam so that the laser intensity at the chalcogenide material is sufficiently high to cause nonlinear optical absorption that causes conversion of input optical energy into supercontinuum laser pulses of a pulse energy at or above a microjoule level at optical wavelengths within a broad continuous mid-infrared spectral range without damaging the chalcogenide material, the motorized actuator operable to move the chalcogenide material laterally relative to the input laser beam so that different portions of the chalcogenide material are exposed to the input laser beam at different times in exposing the chalcogenide material to the input laser beam in generating the supercontinuum laser pulses to avoid damage to the chalcogenide material; and an output beam device in an optical path of the generated supercontinuum laser pulses to direct the generated supercontinuum laser pulses as an optical sensing beam to a target for optically sensing the target.

19. The device as in claim 18, wherein:
the output beam device includes a parabola reflector that reflects and directs the generated supercontinuum laser pulses onto the target.

20. The device as in claim 18, wherein:
the input beam focusing device includes a parabola reflector that reflects and focuses the input laser beam.

21. The device as in claim 18, wherein:
the input beam focusing device includes a lens that focuses the input laser beam, and
the output beam device includes a parabola reflector that reflects and directs the generated supercontinuum laser pulses onto the target.

22. The device as in claim 18, wherein:
the laser source module includes an optical amplifier to produce amplified laser pulses and an optical parametric amplifier that receives the amplified laser pulses to produce the input laser beam having femtosecond pulses at the input laser wavelength and a pulse energy higher than 10 microjoule.

23. The device as in claim 18, wherein:
the motorized actuator is operable to move the chalcogenide material laterally along two directions.

24. The device as in claim 18, wherein:
the motorized actuator is configured to hold the chalcogenide material at a position away from a focus of the input laser beam produced by the input beam focusing device.

25. The device as in claim 18, further comprising:
an optical detector that receives light from the target under illumination of the generated supercontinuum laser pulses to provide optical sensing information on the target.

26. The device as in claim 18, wherein:
the chalcogenide material includes $Ge_{33}As_{12}Se_{55}$, $Ge_{30}As_{13}Se_{32}Te_{25}$, $Ge_{10}As_{40}Se_{50}$, $Ge_{28}Sb_{12}Se_{60}$, or $As_{40}Se_{60}$.

* * * * *